United States Patent [19]

Lantzsch

[11] Patent Number: 4,471,118
[45] Date of Patent: Sep. 11, 1984

[54] PREPARATION OF ALDEHYDES BY HEATING AN α-HYDROXYPHOSPHONIC ACID ESTER

[75] Inventor: Reinhard Lantzsch, Leverkusen, Fed. Rep. of Germany

[73] Assignee: Bayer Aktiengesellschaft, Leverkusen, Fed. Rep. of Germany

[21] Appl. No.: 398,523

[22] Filed: Jul. 15, 1982

[30] Foreign Application Priority Data

Jul. 31, 1981 [DE] Fed. Rep. of Germany ....... 3130431

[51] Int. Cl.³ ............................................. C07C 45/00
[52] U.S. Cl. ................................... 544/335; 546/314; 546/22; 568/420; 568/426; 568/449; 568/485; 568/488; 544/243; 260/937; 260/953
[58] Field of Search ........................ 544/335; 546/314; 568/426, 449, 420, 485, 488

[56] References Cited

U.S. PATENT DOCUMENTS 4,317,783 3/1982 Hoffman ............................. 260/937

FOREIGN PATENT DOCUMENTS 0024611 3/1981 European Pat. Off. .
2917620 11/1980 Fed. Rep. of Germany .

OTHER PUBLICATIONS

Abramov, et al., "J. Gen. Chem.", U.S.S.R., vol. 23, (English translation), pp. 269–271, (1953).
Israel Journal of Chemistry, vol. 4, 1966, pp. 225–231, The Reaction of -Ketophosphonates with Organometallic Compounds and Sodium Borohydride, I. Shahak and E. D. Bergmann.
Israel Journal of Chemistry, vol. 9, 1971, pp. 35–44, Reactions of Dimethyl Benzoylphosphonate, I. Shahak & J. Peretz.
Abramov et al., Chemical Abstracts, vol. 48, p. 2572c.

Primary Examiner—Donald G. Daus
Assistant Examiner—Diana G. Rivers
Attorney, Agent, or Firm—Sprung, Horn, Kramer & Woods

[57] ABSTRACT

A process for the preparation of an aldehyde of the formula

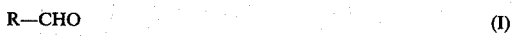

in which R is an optionally substituted alkyl, alkenyl, alkinyl, cycloakyl, cycloalkenyl, aralkyl, aralkenyl, aryl or heteroaryl radical, comprising heating an α-hydroxyphosphonic acid ester of the formula

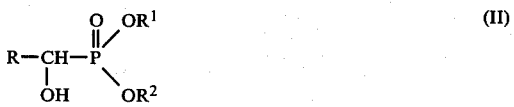

the aldehyde of the formula (I) can be used as an intermediate in the production of pest-combating agents.

6 Claims, No Drawings

PREPARATION OF ALDEHYDES BY HEATING AN α-HYDROXYPHOSPHONIC ACID ESTER

The invention relates to an unobvious process for the preparation of certain aldehydes.

It is already known that aldehydes are obtained if α-oxophosphonic acid esters which have been formed from corresponding carboxylic acid chlorides and trialkyl phosphites are reduced with sodium boranate to give α-hydroxyphosphonic acid esters and the latter are split by means of alkali metal hydroxide solutions (see Chem. Ber. 103 (1970), 2984–2986, or German Offenlegungsschrift No. 2,934,034).

However, the preparation of aldehydes in an alkaline medium suffers from disadvantages owing to the possible side reactions or secondary reactions (for example phosphonate-phosphate rearrangement, aldol reaction or Cannizzaro reaction).

The present invention now provides a process for the preparation of an aldehyde of the general formula $$R-CHO \quad (I)$$

in which
R represents an optionally substituted radical selected from alkyl, alkenyl, alkinyl, cycloalkyl, cycloalkenyl, aralkyl, aralkenyl, aryl and heteroaryl, which is characterized in that an α-hydroxyphosphonic acid ester of the general formula

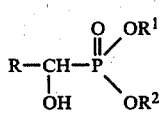

(II)

in which
R has the meaning indicated above and
R[1] and R[2] independently of one another represent an alkyl or phenyl radical or conjointly represent alkanediyl (alkylene), is heated at a temperature between 50° and 300° C., if appropriate in the presence of a diluent.

It must be described as surprising that the aldehydes of the formula (I) can be obtained in very good yields by the process according to the invention by pyrolyzing corresponding α-hydroxyphosphonic acid esters of the formula (II), since a phosphonate-phosphate rearrangement under the influence of heat would have been expected as more probable (compare J. Gen. Chem. USSR 38 (1968), 142–147).

The process according to the invention has various advantages compared with the state of the art. Secondary reactions of aldehydes, which can take place readily in an alkaline medium (aldol reaction, Cannizzaro reaction and the like) are avoided. The phosphorous acid esters which are formed as co-products are not saponified and can be isolated by distillation. The production of effluent is also avoided.

If dimethyl α-hydroxybenzylphosphonate is used as the starting compound, the course of the reaction according to the present invention illustrated by the following equation:

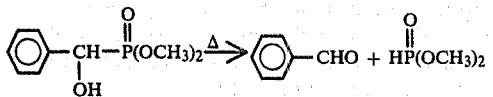

Preferred α-hydroxyphosphonic acid esters of formula (II) to be used as starting materials in the process according to the invention are those, in which
R represents a $C_1$ to $C_5$ alkyl radical which is optionally substituted by fluorine, chlorine, bromine, $C_1$ to $C_4$ alkoxy or $C_1$ to $C_4$ alkylthio; a $C_3$ to $C_5$ alkenyl or $C_3$ to $C_5$ alkinyl radical which is optionally substituted by fluorine, chlorine or bromine; a $C_3$ to $C_6$ cycloalkyl radical which is optionally substituted by fluorine, chlorine, bromine, $C_{1\text{-}4}$-alkyl, $C_1$ to $C_4$ alkylcarbonyl, $C_1$ to $C_4$ alkoxy-carbonyl, phenoxybenzyloxycarbonyl (which is optionally substituted by fluorine, chlorine, bromine, methyl, methoxy and/or cyano) and/or cyano, benzyl or phenylethyl which is optionally substituted by chlorine, $C_1$ to $C_4$ alkyl and/or trifluoromethyl; or a phenyl, pyridinyl or pyrimidinyl radical which is optionally substituted by nitro, fluorine, chlorine, bromine, $C_1$ to $C_4$ alkyl, trifluoromethyl, $C_1$ to $C_4$ alkoxy, trifluoromethoxy, $C_1$ to $C_4$ alkylthio, trifluoromethylthio, $C_1$ or $C_2$ alkylenedioxy (which is optionally substituted by fluorine) and/or phenoxy (which is optionally substituted by fluorine, chlorine, bromine, $C_1$ to $C_4$ alkyl, trifluoromethyl, $C_1$ to $C_4$ alkoxy, trifluoromethoxy, $C_1$ to $C_4$ alkylthio, trifluoromethylthio and/or $C_1$ to $C_4$ alkylenedioxy),
$R^1$ represents a $C_1$ to $C_4$ alkyl or phenyl radical and
$R^2$ represents a $C_1$ to $C_4$ alkyl or phenyl radical or, together with $R^1$, represents straight-chain or branched $C_2$ to $C_5$ alkanediyl radical.

Starting compounds of the formula (II) are known. They can be prepared by processes which are in themselves known by reducing corresponding α-oxophosphonic acid esters (see Houben-Weyl, Methoden der organischen Chemie ("Methods of organic chemistry"), 4th edition, volume 12/1, page 512, Thieme-Verlag, Stuttgart 1963; Israel J. Chem. 4(1966), 255; ibid.9 (1971), 33; German Offenlegungsschrift No. 2,917,620 and German Offenlegungsschrift No. 2,934,034).

The following may be mentioned as examples of the starting compounds of the formula (II):
dimethyl and diethyl α-hydroxyethylphosphonates, α-hydroxy-n-propylphosphonates, α-hydroxy-n-butylphosphonates, α-hydroxy-isobutylphosphonates, α-hydroxy-n-pentylphosphonates, α-hydroxy-isopentylphosphonates, α-hydroxy-neopentyl-phosphonates, (α-hydroxy-β,β-dimethylpropyl)-phosphonates, α-hydroxybenzylphosphonates, α-hydroxy-3-methylbenzylphosphonates, α-hydroxy-4-methylbenzylphosphonates, α-hydroxy-3,4,-dimethylbenzylphosphonates, α-hydroxy-4-ethylbenzylphosphonates, α-hydroxy-4-isopropylbenzyl-phosphonates, α-hydroxy-4-tert.-butylbenzylphosphonates, α-hydroxy-4-fluorobenzylphosphonates, α-hydroxy-4-chlorobenzylphosphonates, α-hydroxy-2,4-dichlorobenzylphosphonates, α-hydroxy-4-bromobenzylphosphonates, α-hydroxy-3-bromo-4-fluorobenzylphosphonates, α-hydroxy-4-methoxy-benzylphosphonates, α-hydroxy-3,4-dimethoxybenzylphosphonates, α-hydroxy-2-trifluoromethylbenzylphosphonates, α-hydroxy-3-trifluoromethylbenzylphosphonates, α-hydroxy-4-trifluoromethylbenzylphosphonates, α-hydroxy-3-phenoxy-benzylphosphonates, α-hydroxy-4-fluoro-3-phenoxybenzylphosphonates and α-hydroxy-4-trifluoromethoxybenzylphosphonates; and also dimethyl and diethyl α-hydroxy-α-(2,2-dichloro-1-methylcyclopropyl)-methanephosphonates, α-hydroxy-α-(3-methoxycarbonyl-2,2-dimethylcyclopropyl)-methanephosphonates, α-hydroxy-α-(3-ethoxycarbonyl-2,2-dimethylcyclopropyl)-methanephosphonates and α-hydroxy-α-(3-cyano-2,2-dimethylcyclopropyl)-methanephosphonates.

The process according to the invention is carried out without a diluent or in the presence of a diluent. Suitable diluents are preferably inert organic solvents. These include, in particular, optionally halogenated hydrocarbons (such as toluene, xylene, chlorobenzene, dichlorobenzene and decalin), and ethers (such as glycol dimethyl ether and diglycol dimethyl ether).

In carrying out the process according to the invention, the reaction temperature is within the specified fairly large range of 50° and 300° C., preferably between 100° and 250° C. and especially between 150° and 200° C.

In carrying out the process according to the invention, the pressure can also be varied within a fairly large range. In general, the reaction is carried out within the range between 0.0001 and 2,000 mbars, preferably between 0.01 and 1,500 mbars.

The process according to the invention can be carried out by customary methods or pyrolysis.

In a preferred embodiment, the process is carried out in a distillation apparatus which has, if necessary, been preheated to the reaction temperature required, and into which the starting compound of the formula (II), if appropriate dissolved in a diluent, is metered in, while at the same time the product of the formula (I) and, if appropriate, the phosphorous acid ester formed as the co-product and the diluent are removed by distillation, if appropriate under reduced pressure. It is also possible to introduce the whole of the starting material of the formula (II) initially into the apparatus and to bring it gradually to the reaction temperature required, the products also being isolated by distillation.

In carrying out the process, it is essential to remove the aldehyde which has been formed as rapidly as possible from the reaction mixture. If required, the products can be purified by a further (fractional) distillation.

Some of the compounds which can be prepared in accordance with the invention can be used, for example, as intermediate products for pest-combating agents (see German Offenlegungsschrift No. 2,934,034).

PREPARATIVE EXAMPLES

Example 1

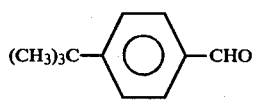

27.2 g (0.1 mol) of dimethyl α-hydroxy-4-tert.-butylbenzylphosphonate were dissolved in 25 ml of toluene and were added dropwise, from a dropping funnel, into a distillation apparatus which had been preheated to 180° C. and had a small Vigreux column to which a water pump vacuum was applied. The distillate was fractionally distilled in a high vacuum. 13.8 g (81.5% of theory) of 4-tert.-butylbenzaldehyde of boiling point 72° C./0.15 mbars were obtained.

Example 2

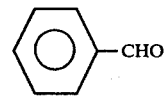

122 g (0.5 mol) of diethyl α-hydroxybenzylphosphonate were heated at 165°–190° C./12 mbars in a distillation apparatus, under a water pump vacuum. 78 g of distillate, consisting, according to gas chromatography, of 58% of benzaldehyde and 38.5% of diethyl phosphite distilled over. This corresponded to a yield of benzaldehyde of 85.4% of theory. The yield could be increased to over 95% by carrying out the process with the aid of a thin film evaporator.

Example 3

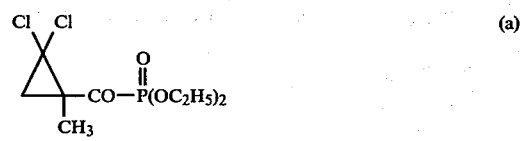

69 g (0.368 mol) of 2,2-dichloro-1-methylcyclopropane-1-carboxylic acid chloride were added dropwise at room temperature to 61 g (0.368 mol) of triethyl phosphite. The mixture was stirred for a further hour and the readily volatile constituents were removed by distillation in a high vacuum at 50° C. The residue consisted of 127 g of diethyl 2,2-dichloro-1-methylcyclopropylcarbonylphosphonate (a colorless oil).

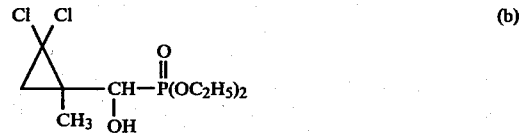

28.9 g (0.1 mol) of diethyl 2,2-dichloro-1-methylcyclopropylcarbonylphosphonate and 1 g of tetrabutylammonium bromide were initially introduced into 100 ml of toluene, and 1.134 g (0.03 mol) of sodium boranate in 20 ml of water were added dropwise at 15° to 20° C. After stirring for a further hour, the mixture was neutralized and the toluene phase was separated off, washed with water, dried and concentrated. This gave 24.4 g of a colorless oil, which solidified after a little time. Melting point 57° C.

20 g (0.0687 mol) of dimethyl α-hydroxymethyl-(2,2-dichloro-1-methylcyclopropyl)-phosphonate prepared analogously to (a) and (b) sugars, were distilled under a water pump vacuum. 17.4 g of a product consisting of 49.5% of dimethyl phosphite and 43.6% of 2,2-dichloro-1-methyl-1-formylcyclopropane distilled over at 170° to 180° C./12 mbars. The aldehyde was obtained in a pure state by fractional distillation, boiling point 68° C./18 mbars.

Example 4

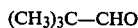

31 g (0.138 mol) of diethyl α-hydroxyneopentylphosphonate were heated at 180° to 190° C. under normal pressure in a distillation apparatus; the distillate (65° to 80° C.) (10.2 g) consisted of 97.6% of dimethylpropionaldehyde. Yield: 83.4% of theory.

Example 5

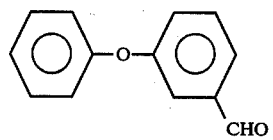

59 g of diethyl 3-phenoxy-α-hydroxybenzylphosphonate were dissolved in 150 ml of toluene and added dropwise to a distillation apparatus which had been preheated to 220° C. and to which a water pump vacuum was applied. A mixture of toluene, diethyl phosphite and 3-phenoxybenzaldehyde distilled over. 33.2 g (83.8% of theory) of pure 3-phenoxybenzaldehyde of boiling point 138° to 145° C./0.1 mbar were obtained by fractional distillation.

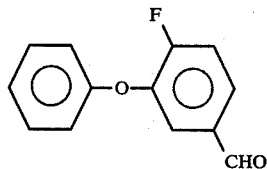

3-phenoxy-4-fluorobenzaldehyde was obtained in 85% yield analogously to the above example.

Example 6

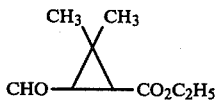

30.8 g (0.1 mol) of ethyl 2,2-dimethyl-3-(hydroxydiethylphosphonyl)-methylcyclopropane-1-carboxylate were heated at 180° to 200° C. in a distillation apparatus. 28.7 g of product distilled over at this temperature and under a pressure of 12 mbars, and were redistilled again. 14.8 g (87% of theory) of caronaldehyde, of boiling point 61° to 65° C./0.1 mbar, were obtained.

It was possible to obtain the following compounds analogously to the examples described above:

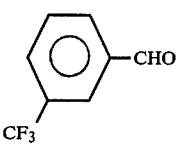

Yield 87%.
Boiling point: 72°-74° C./15 mbars.

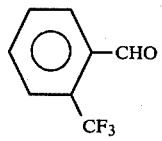

Yield: 81%.
Boiling point: 62°-65° C./15 mbars.

It will be appreciated that the instant specification and examples are set forth by way of illustration and not limitation, and that various modifications and changes may be made without departing from the spirit and scope of the present invention.

I claim:
1. In the preparation of an aldehyde of the formula

in which R is an optionally substituted alkyl, alkenyl, alkinyl, cycloalkyl, cycloalkenyl, aralkyl, aralkenyl, aryl or heteroaryl radical, by heating an α-hydroxyphosphonic acid ester of the formula

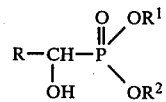

in which $R^1$ and $R^2$ each independently is an alkyl or phenyl radical or conjointly are an alkanediyl (alkylene) radical, the improvement which comprises effecting the heating at a temperature between about 50° and 300° C. in the absence of a basic catalyst.

2. A process according to claim 1 in which
R represents a $C_1$ to $C_5$ alkyl radical which is optionally substituted by fluorine, chlorine, bromine, $C_1$ to $C_4$ alkoxy or $C_1$ to $C_4$ alkylthio; a $C_3$ to $C_5$ alkenyl or $C_3$ to $C_5$ alkinyl radical which is optionally substituted by fluorine, chlorine or bromine; a $C_3$ to $C_6$ cycloalkyl radical which is optionally substituted by fluorine, chlorine, bromine, $C_1$ to $C_4$ alkyl, $C_1$ to $C_4$ alkylcarbonyl $C_1$ to $C_4$ alkoxycarbonyl, phenoxybenzyloxycarbonyl (which is optionally substituted by fluorine, chlorine, bromine, methyl, methoxy, and/or cyano), benzyl or phenylethyl which is optionally substituted by chlorine, $C_1$ to $C_4$ alkyl and/or trifluoromethyl; or a phenyl, pyridinyl or pyrimidinyl radical which is optionally substituted by nitro, fluorine, chlorine, bromine, $C_1$ to $C_4$ alkyl, trifluoromethyl, $C_1$ to $C_4$ alkoxy, trifluoromethoxy, $C_1$ to $C_4$ alkylthio, trifluoromethylthio, $C_1$ or $C_2$ alkylenedioxy (which is optionally substituted by fluorine) and/or phenoxy (which is optionally substituted by fluorine, chlorine, bromine, $C_1$ to $C_4$-alkyl, trifluoromethyl, $C_1$ to $C_4$ alkoxy, trifluoromethoxy, $C_1$ to $C_4$ alkylthio, trifluoromethylthio, and/or $C_1$ to $C_4$ alkylendioxy),
$R^1$ represents a $C_1$ to $C_4$ alkyl or phenyl radical and
$R^2$ represents a $C_1$ to $C_4$ alkyl or phenyl radical or, together with $R^1$, represents a straight-chain or branched $C_2$ to $C_5$ alkanediyl radical.

3. A process according to claim 1, wherein the reaction is carried out in the presence of a diluent.

4. A process according to claim 3, wherein the diluent is an inert organic solvent.

5. A process according to claim 1, wherein the reaction is carried out at a temperature between about 105° and 220° C.

6. A process according to claim 2, wherein the reaction is carried out at a temperature between about 150° and 220° C. in the presence of an inert organic solvent as diluent.

* * * * *